(12) United States Patent
Wasserman et al.

(10) Patent No.: US 7,131,996 B2
(45) Date of Patent: Nov. 7, 2006

(54) ARTIFICIAL URINARY DIVERSION DEVICE

(76) Inventors: Helmut Wasserman, Struwwelpeterstrasse 5B, München (DE) D-81739; Dieter Jocham, Zwinglistrasse 1, Lübeck (DE) D-23568

( * ) Notice: Subject to any disclaimer, the term of this patent is extended or adjusted under 35 U.S.C. 154(b) by 0 days.

(21) Appl. No.: 10/101,652

(22) Filed: Mar. 20, 2002

(65) Prior Publication Data

US 2002/0193884 A1 Dec. 19, 2002

Related U.S. Application Data

(63) Continuation-in-part of application No. 09/936,721, filed as application No. PCT/EP00/02407 on Mar. 17, 2000.

(30) Foreign Application Priority Data

Mar. 18, 1999  (DE) ................................ 199 12 218
Mar. 19, 1999  (DE) ................................ 199 12 472

(51) Int. Cl.
*A61F 2/04* (2006.01)
(52) U.S. Cl. .................................. 623/23.65
(58) Field of Classification Search ............. 623/11.11, 623/23.64, 23.65
See application file for complete search history.

(56) References Cited

U.S. PATENT DOCUMENTS

| | | | |
|---|---|---|---|
| 4,044,401 A * | 8/1977 | Guiset ..................... | 623/23.65 |
| 4,228,550 A * | 10/1980 | Salkind .................... | 623/23.66 |
| 4,256,093 A | 3/1981 | Helms et al. | |
| 4,311,659 A | 1/1982 | Rey et al. | |
| 4,976,735 A | 12/1990 | Griffith et al. | |
| 5,041,136 A | 8/1991 | Wascher et al. | |
| 5,092,886 A * | 3/1992 | Dobos-Hardy ........... | 623/23.65 |
| 5,147,388 A | 9/1992 | Yamazaki | |
| 5,304,114 A * | 4/1994 | Cosman et al. ................. | 604/8 |
| 5,785,641 A | 7/1998 | Davis | |
| 5,813,410 A | 9/1998 | Levin | |
| 6,366,814 B1 | 4/2002 | Boveja et al. | |

FOREIGN PATENT DOCUMENTS

| | | |
|---|---|---|
| DE | 24 61 627 | 7/1975 |
| DE | 27 60 437 C2 | 10/1977 |
| DE | 26 55 034 | 6/1978 |
| DE | 35 26 164 A1 | 1/1987 |
| DE | 39 32 718 A1 | 4/1991 |
| DE | 195 44 162 C1 | 11/1995 |
| WO | WO 93/16659 | 9/1993 |
| WO | WO 95/11637 | 5/1995 |
| WO | WO 98/35633 | 8/1998 |

* cited by examiner

*Primary Examiner*—Corrine McDermott
*Assistant Examiner*—Christopher Prone
(74) *Attorney, Agent, or Firm*—Lerner, David, Littenberg, Krumholz & Mentlik, LLP (57) ABSTRACT

An artificial urinary diversion device containing a urinary bladder is provided including first, second and third portions having respective cross-sectional surfaces such that the second portion is disposed between the first and third portions, and the first and second cross-sectional surfaces are smaller than the third cross-sectional surfaces, and a dislocator for sensing or controlling the artificial urinary diversion device.

8 Claims, 13 Drawing Sheets

ARTIFICIAL URINARY DIVERSION DEVICE

CROSS-REFERENCE TO RELATED APPLICATIONS

This application is a continuation-in-part of U.S. patent application Ser. No. 09/936,721, filed Dec. 19, 2001, which is a 371 of PCT/EP00/02407, filed on Mar. 17, 2000.

FIELD OF THE INVENTION

The present invention relates to an artificial urinary diversion device. More particularly, the present invention also relates to a suitable method for implantation of a artificial urinary diversion device.

BACKGROUND OF THE INVENTION

Among patients with urinary bladder disorder there are a plurality of findings which require removal of the patient's bladder. In this situation, a urinary diversion incorporating different types of reservoirs is generally required. So-called wet diversions are preferred, with direct urinary diversion through the ureters, which are implanted into the abdominal wall, or by insertion of a neutralized part of the intestine, in which the ureters are implanted and which is for its part implanted into the abdominal wall.

In both cases the urine is collected in a urine bag, which is attached to the orifice.

Alternatively, the ureters are implanted into the rectum or—more and more in the past several years—into replacement bladders, which are made of neutralized parts of the intestine.

These replacement bladders are either connected with the endogenous urethra or they are conducted out by creating an appropriate self-preserving occlusion mechanism at the abdominal skin, for example in the navel region.

Typical indicators for a replacement of the endogenous urinary bladder are advanced tumors of the urinary bladder, but there are also malformations, bladder impairments due to inflammation, as well as functional obstructions, such as for example obstructions by urinating, or development of bladder atrophies among paraplegics.

Thus, one of the objects of the present invention is to create an artificial urinary diversion system and a suitable method for implanting same which is adaptable to the different shapes of different persons, which shows the largest possible filling volume, and which allows for easy handling.

It is another object of the present invention to create an artificial urinary diversion system which is highly adaptable, and which without previous direct or indirect determination of the potentially available volume for such a system, facilitates as effective as possible a determination of the volume available in the patient during surgery, and thus utilization of this device therein.

SUMMARY OF THE INVENTION

In accordance with the present invention, these and other objects have now been realized by the invention of an artificial urinary diversion device containing a urinary bladder, an axial direction, and comprising at least one first portion having a first cross-sectional surface perpendicular to the axial direction and including at least one outlet, a second portion having a second cross-sectional surface perpendicular to the axial direction, and a third portion having a third cross-sectional surface perpendicular to the axial direction, and including at least one inlet for accommodating the urinary bladder, the second portion being arranged between the first portion and the third portion, the first and second cross-sectional surfaces being smaller than the third cross-sectional surface. In a preferred embodiment, the artificial urinary diversion device also includes a dislocation device for sensing or controlling the artificial urinary diversion device. Preferably, the first, second and third portions comprise modular units, whereby each of the first, second and third portions includes a transitional surface permitting a continuous surface transition between the modular units.

In accordance with one embodiment of the artificial urinary diversion device of the present invention, the first cross-sectional surface is larger than the second cross-sectional surface.

In accordance with another embodiment of the artificial urinary diversion device of the present invention, the device includes fluid guidance means for guiding fluid from the urinary bladder through the third portion, the second portion, and the first portion.

In accordance with another embodiment of the artificial urinary diversion device of the present invention, the device includes an actuator for actuating the urinary bladder. Preferably, the actuator comprises a pump, and the pump is preferably disposed in the third portion. In a preferred embodiment, the pump comprises a telescopic device, and in another embodiment, the pump comprises a lever pump including two chambers. In yet another embodiment, the pump comprises a screw pump. Preferably, the screw pump is disposed in the first portion. In another embodiment, the screw pump includes at least one screw which can be moved laterally.

In accordance with another embodiment of the artificial urinary diversion device of the present invention, the device includes a sphincter mechanism. Preferably, the sphincter mechanism is disposed in the first portion.

In accordance with another embodiment of the artificial urinary diversion device of the present invention, where the dislocation device is utilized, it includes control means. Preferably, the device includes a sphincter mechanism, and control means are provided for controlling the sphincter mechanism. In another embodiment, the device includes a pump, and the control means controls the pump. Preferably, the device includes secondary batteries, and the control means controls the recharge of the secondary batteries.

In accordance with another embodiment of the artificial urinary diversion device of the present invention, the device includes a sensor system for monitoring the filling level of the urinary bladder. In the preferred embodiment, the device includes signal means whereby the sensor system produces a signal when reaching a predetermined filling level of the urinary bladder. Preferably, the signal comprises an audible or a vibratory signal. Preferably, the sensor system is controlled by the nerves responsible for natural urinary bladder control.

In accordance with another embodiment of the artificial urinary diversion device of the present invention, the device includes a power supply. In a preferred embodiment, the device includes an external recharge device whereby the external recharge device cooperates with the power supply. Preferably, the external recharge device cooperates inductively with the power supply. In one embodiment, the power supply comprises secondary batteries integrated into the artificial urinary diversion device. In another embodiment, the power supply comprises primary batteries integrated into the artificial urinary diversion device. Preferably, the external recharge device is disposed in the dislocation device. In a preferred embodiment, the dislocation device includes a display for indicating the dislocation. Preferably, the display includes a level indicator. In a preferred embodiment, the dislocation device comprises an abdominal bandage and includes a separate control mechanism. In accordance with one embodiment, the dislocation device is integrated into a garment. In another embodiment, the apparatus includes an ultrasonic transmitter and a receiver device for controlling the display. Preferably, the ultrasonic transmitter and receiver device includes external Reed contacts, a Hall generator, and a charging current unit of measurement or a power sensor.

In accordance with another embodiment of the artificial urinary diversion device of the present invention, the device includes an actor system for executing the removal of urine from the artificial urinary diversion device.

In accordance with another embodiment of the artificial urinary diversion device of the present invention, the third portion is divided into two parts which can be separated from each other depending on the filling level of the urinary bladder.

In accordance with another embodiment of the artificial urinary diversion device of the present invention, the third portion includes either one or two inlets.

In accordance with another embodiment of the artificial urinary diversion device of the present invention, the device includes at least one anti-reflux valve. Preferably, the at least one anti-reflux valve is disposed in the third portion.

In accordance with another embodiment of the artificial urinary diversion device of the present invention, the device includes a fixing element. In a preferred embodiment, the device includes a dovetail joint, and the fixing element is connected with the artificial urinary diversion device by means of the dovetail joint. In another embodiment, the device includes guide-rail means whereby the fixing element can be removably included and locked at a predetermined position. Preferably, the guide-rail means is integrated into the third portion. In another embodiment, the fixing element comprises a splay or expanding element. In accordance with a preferred embodiment, the fixing element is entirely included therewithin. In another embodiment, the fixing element is composed of a biocompatible, elastic material, preferably silicone.

In accordance with another embodiment of the artificial urinary diversion device of the present invention, the device includes a first outline of a shape corresponding to a polynomial function of $6^{th}$ degree, wherein $$F(x)=A+a_1x+a_2x^2+a_3x^3+a_4x^4+a_5x^5+a_6x^6$$

in which $0<A<2$; $0<a_1<8$; $-2<a_2<0$; $0<a_3<1$; $-0,1<a_4<0$; $0<a_5<0,003$; and $-0,00001<a_6<0$, within the domain in which $0<x<22$.

In accordance with another embodiment of the artificial urinary diversion device of the present invention, the device includes a second outline of a shape corresponding to a polynomial function of $6^{th}$ degree, wherein $$F(x)=A+a_1x+a_2x^2+a_3x^3+a_4x^4+a_5x^5+a_6x^6$$

in which $0<A<2$; $0<a_1<8$; $-2<a_2<0$; $0<a_3<1$; $-0,1<a_4<0$; $0<a_5<0,003$; and $-0,00001<a_6<0$ within the domain in which $0<x<22$.

In accordance with another embodiment of the artificial urinary diversion device of the present invention, the first, second and third portions are formed integrally. Preferably, the third portion includes an originating electric link to a portion of the dislocation device which is subcutaneously implanted.

In accordance with one embodiment of the artificial urinary diversion device of the present invention, the actor is controlled by an encoded signal.

In accordance with the present invention, a method has also been provided for implanting the artificial urinary diversion device discussed above, the method including the steps of selecting a modular unit which has an external contour corresponding to the artificial urinary diversion device; exchanging the modular unit for one of the first, second or third portions to obtain a matching implantable artificial urinary diversion device; assembling the artificial urinary diversion device in correspondence with the modular unit; and implanting the assembled artificial urinary diversion device.

According to the present invention, the second area, which is arranged between the first and the third area, includes a cross-sectional surface which is smaller than the cross-sectional surface of the third area. In this manner, a shape is provided, which can be adapted to almost any patient, and more particularly, the largest possible filling volume can be provided, namely by simultaneous consideration of various medical preconditions, such as for example the arteries and the intestine that, after the operation, pass laterally to the second area and on which no pressure must be put. Attention must be paid to the fact that, with a person who is standing erect, the third area is arranged above the second area and the first area. For example, if the first area shows a larger cross-sectional surface than the second area, a so-called constriction will also be provided in the second area, which is necessary for the bypassing arteries and/or the intestine and the kidneys, and a positional fixing with the first area is possible, for example, at the pubic bone (Symphysis Pubica). With the dislocation device, according to the present invention, which may, for example, be a device for dislocation supervision or dislocation display, handling of the device will be eased during permanent use thereof. By utilizing the dislocation device, on the one hand, it is possible to indicate the position for the optimal wireless transcutaneously transfer of performance or, on the other hand, to describe a support when correcting the positioning in case of an initial false placing, as each dislocation leads to a loss of performance.

With the method according to the present invention, implantation of an artificial urinary diversion system is provided, which, due to the provision of an element or module which possesses the external contour of the artificial urinary diversion system, and which can be assembled in a modular design, protection of the patient and of the resources is possible. Therefore, in a first step in the operating room, a plurality of sample pieces, i.e., modules of the element, are assembled to an optimally suited urinary diversion system for the patient. Thus, especially with regards to hygiene, a method is provided which only requires sterilization of the particular modules of the element, and not, in the case of mismatching, modules with a highly complicated technique inside.

If the first, second and third areas are modularly compounded or rendered modularly compoundable, and if the respective transition surfaces between the individual areas are coordinated in a desired manner, a continuous transition results, and the advantage will be achieved that, according to the respective spatial condition of the patient, the individual areas of the urinary diversion system can be compounded and thus, it will be possible to take optimal account of the anatomical conditions of the patient.

If fluid guidance means are provided, which extend from the urinary bladder to the outlet in the first area, this corresponds to a large extent to the natural anatomy, which means, that among a person who is standing erect, the lowest, first area can be connected directly with the existing urethra, without using additional connection elements between the urethra and the outlet in the first area, which could possibly cause further medical complications.

If an actor or an actuator or a pump is provided in the third area, there is then no need to provide an external pump, and, in view of the shape selected, the first and second areas are not negatively influenced. Furthermore, in the embodiment in which an actuator or a pump is provided in the third area, the third area, which is optimally embodied, can now be most likely to have the most space for the integration of a pump without greatly or negatively influencing the shape.

If the pump is formed as a telescope device, almost the total volume of the third area can now be advantageously used for filling the urinary bladder. Laboratory experiments have already shown that almost the entire urinary bladder can be emptied with a telescope device, without leaving any sediment in the urinary bladder.

If the pump is formed as a lever pump, no complex mechanics are required to be integrated therein, such as for example for the use of a telescope device in the third area.

If the pump is formed as a screw pump, another advantage is that almost the entire volume of the third area can now be used for the urinary bladder. In addition, by using a screw pump, the screw pump can pulverize possible smaller urine crystals, so that these pulverized crystals can also be passed through a stenotic urethra.

If additionally a screw pump is also arranged, such that it may possibly be displaced laterally to the fluid tube or duct, an inlet and a lavage of the artificial urinary diversion system can now be provided without difficulty, since the fluid tube can now be opened by moving the screw. This result concerning the inlet and the lavage of the artificial urinary diversion system can be very important in the field of spectroscopic examinations, for example.

If a sphincter mechanism is preferably provided in the first area, almost total control of the urinary continency is now possible. The control of the sphincter mechanism can, for example, also be initiated externally.

If, in addition, a control system is provided, which regulates the sphincter mechanism, such a control system, which is also able to assume further procedures, can also regulate opening and closing of the sphincter.

If, a sensor system is provided for controlling the filling level of the urinary bladder, the patient will be given a high degree of safety by using the artificial urinary bladders. That is, the patient does not have to void the urinary bladder regularly and in short intervals, but can instead integrate with everyday life in the usual way. If either a sound signal or a seismic signal, which will be produced at a certain filling level of the bladder, is sent to the concerned person, the person can operate normally in everyday life. However, it is also noted that, if at least a security regulation is installed in the sensor system, then, if a certain period of time, for example 8 to 12 hours, is exceeded, the person is signaled to void the bladder, independent of the filling level of the bladder. Furthermore, by controlling the filling level of the artificial bladder security is provided, which is oriented for specific physiological marginal conditions. Thus, the artificial urinary diversion system can operate similarly to the function of the natural urinary bladder. Thus, with this urinary diversion system similar to the natural process, the body first signals the person that the urinary bladder should be emptied, then the bladder will be opened, the urine will be pressed out or squeezed out, and the bladder will be closed again.

If the sensor system is controlled by the nerves responsible for the urinary bladder, an almost natural feeling will be given to the concerned person by means of this neurological solution, and therefore an exogenous signal, such as that produced by a sound signal, or a seismic signal, will not be necessary.

If a power supply is additionally provided in the urinary diversion system, a compact urinary diversion device can be provided, which can, for example, first be integrated into the artificial urinary diversion system. However, the power supply can also be arranged separately, near the urinary diversion system in the patient, if, for reasons of space, a third area must be used which does not allow for an additional power supply.

If an external recharge device provides the power supply, the urinary diversion system can be provided with power for almost a lifelong period. Charging of the counterpart of the external recharge device can be effected by the adapted counterpart, which is charging wireless transcutaneously at an adapted main support location, which is implanted subcutaneously.

A simple power transfer can, for example, be achieved by the recharge device cooperating inductively with its counterpart, with power being transferred inductively at frequencies which are tolerated by the body, for example 30 kHz.

If the power supply is composed of secondary batteries, the urinary diversion system will optimally cooperate with the recharge device.

If the power supply is comprised of primary batteries, which are integrated into the urinary diversion device, the urinary diversion device will work without any continuing maintenance and the person concerned does not have to worry about the power supply.

If the dislocation unit is integrated into the recharge device, handling is simplified and, when the recharge device is out of place, such false placement will be documented. This is quite important, because, in case of inductive, capacitive or other wireless transmission of performance data from the outside into the human body, the external and internal transmitter components must be optimally led together in the appropriate position. In this manner, direct positioning can be shown digitally by means of a yes/no display or an optimal/non-correct display.

If the dislocation unit includes a display unit for indicating dislocation, preferably a level display, the extent of longitudinal dislocation and the extent of rotational dislocation, particularly by means of a level display, are shown.

If the dislocation unit is developed as an abdominal bandage with a separate operating element, a compact system is provided, which can be worn partially invisibly and permanently correctly positioned.

If the dislocation unit is integrated into a garment, the user can comply with his habits, without being visibly singled out.

Identification of improper positioning can be effected alternatively, or it can be combined by means of an ultrasonic transmitter and receiver with an attaching telemetric data-signal transmission from the body, or an external reed contact, which react with a subcutaneously implanted magnetic field of, for example, at least two permanent magnets, or by means of a Hall generator or an agitated Hall sensor, which reacts with implanted magnetic or field-producing components, or by means of a charging-current measurement, whose correct positioning of the transmission media results in a maximum charging current, as lateral deviations in any direction and in rotation diminish the ideal position of the charging current, whereby by measuring and indicating the charging current correct positioning can be determined, or this can be done by means of a current sensor.

If an actor system is also integrated into the urinary diversion device, once again a completely independent system can be provided, which only needs to be connected at the inlets or outlets with functional structures of the patient's urinary diversion system, and which can be implanted as one compact part.

It is also pointed out that where necessary the power for the actor system and/or the sensor system can be transferred wirelessly transcutaneously by placing a suitable transfer device onto the skin. However, it is also necessary in that case that controlling and providing can also be executed by primary batteries as an additional power source. It is also possible that the total control and sensor system can be interrogated, and initiated externally telemetrically.

If the third area is constructed bipartite or in two-part form and dependent on the filling level of the urinary bladder, one part is able to move away from the other part, it is also possible to flexibly adjust the size of the urinary bladder and the filling level, in accordance with the patient's requirements.

If the urinary diversion device includes two inlets in the third area, so that each ureter can be connected with the artificial urinary diversion system, it will not be necessary to provide a further separate additional element, for example in a Y-shape, which can be used if it is advantageous that the urinary diversion device only has one inlet.

By providing one or more anti-reflux valves in the third area, reflux of the urine into the kidney can be stopped. This also prevents possible ascent of bacteria from the bladder up to the kidney.

If a fixing element is provided, it is then easy to arrange and fix it in the human body.

If the fixing element is connected with the urinary diversion device by means of a dovetail joint, a tight or leak-proof connection can be constructed, and the fixing element can be retained in the body, in order to be later connected at the right place with the urinary diversion device.

If the fixing element is movably fixed by means of a guidance system, the urinary diversion device can, according to the anatomy of the person concerned, be optimally arranged and fixed. If the guide-rail system is also integrated into the third area, there are no rails available that are protruding from the third area, which could possibly adversely influence arrangement in the human body, or cause any functional or spatial inconvenience.

If the fixing element includes a splay or expanding element, which may, for example, widen after implanting into the guide rails, the possibility of a simple connection is provided, guarantying a particular compatibility by the complete integration of the splay element into the fixing element.

If the fixing element is formed with a biocompatible material, such as silicone, a well-tolerated material is provided, and in addition the elasticity of the silicone and other such materials are utilized due to the splay movements of the splay element.

If the actor is controlled by an encoded signal, a malfunction of different artificial urinary diversion systems is impossible, thus avoiding any unintentional voiding of different artificial urinary diversion systems.

BRIEF DESCRIPTION OF THE DRAWINGS

Referring to the following detailed description, which refers to the drawings, the artificial urinary diversion system of the present invention is described in detail, as follows.

DETAILED DESCRIPTION

Figure 1:
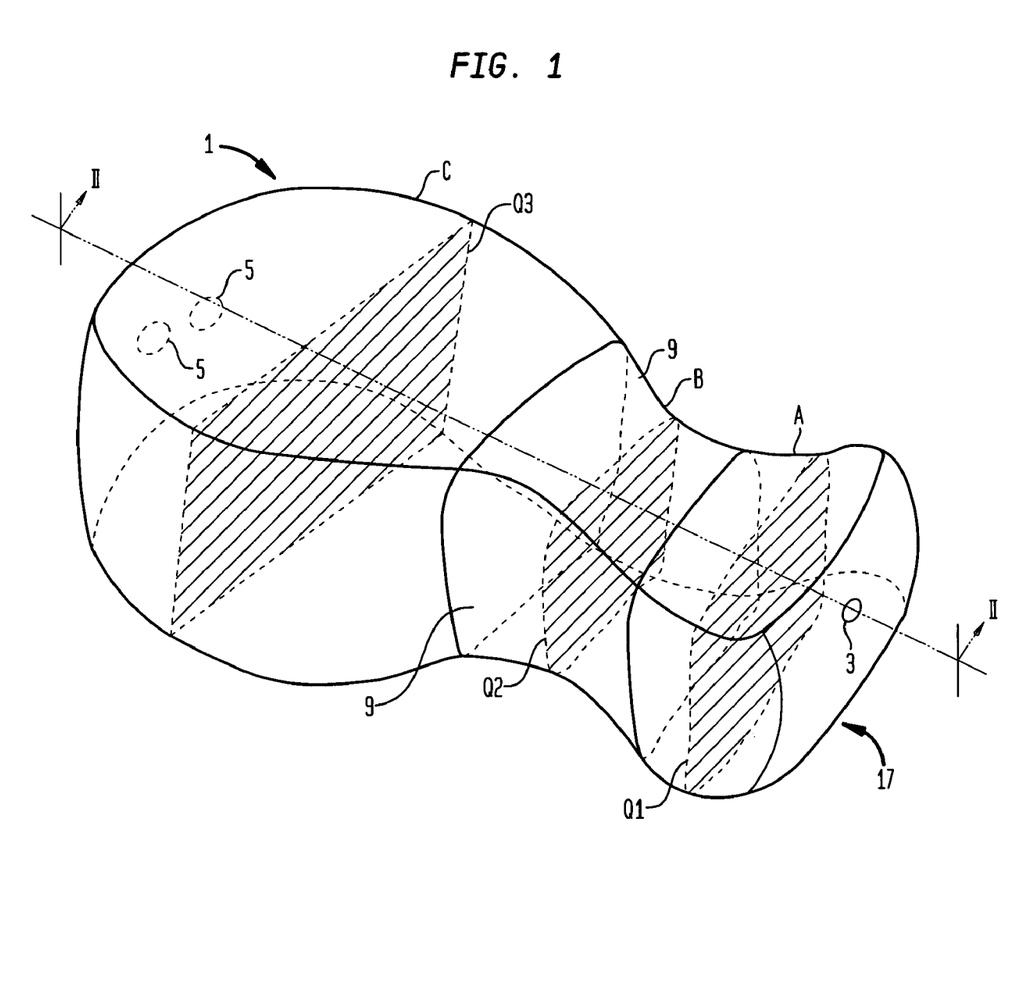
FIG. 1 is a side, perspective, schematic view of the artificial urinary diversion system of the present invention.

A preferred embodiment of the urinary diversion system explained in FIG. 1 includes a first area A, a second area B and a third area C, with the cross-sectional surfaces (illustrated hatched) that are perpendicular to the axial alignment of the urinary diversion device of the first, second and third areas, being constructed such that the cross-sectional surface Q1 of the first area A is larger than the cross-sectional surface Q2 of the second area B and the cross-sectional surface Q3 of the third area C is in each case larger than the cross-sectional surfaces of the first and second areas. In addition, the first area A includes an outlet 3 and the third area C includes two inlets 5 for the urethras, which come from the respective kidneys.

The first area A of the urinary diversion system includes at its bottom surface 7 an increasing area D, with the shape possibly being linear, arched, concave or convex, dependent upon the patient's anatomical conditions for the urinary diversion system hereof. In FIG. 1 it can clearly be seen that the second area B, which is arranged between the first area and the third area, is to be regarded as a constriction, with arteries being led by laterally to its surfaces 9. The third area C, which comprises a urinary bladder, is shaped voluminously enough to allow for filling as much as possible. The two inlets for the renal urethra are provided at the front side of the third area. The third area C also includes an activator or actor, such as a conventional pump 20 (see FIG. 2), which can pump the fluid through the urinary bladder in the direction shown by the arrows thereon, upon activation thereof.

Figure 2:
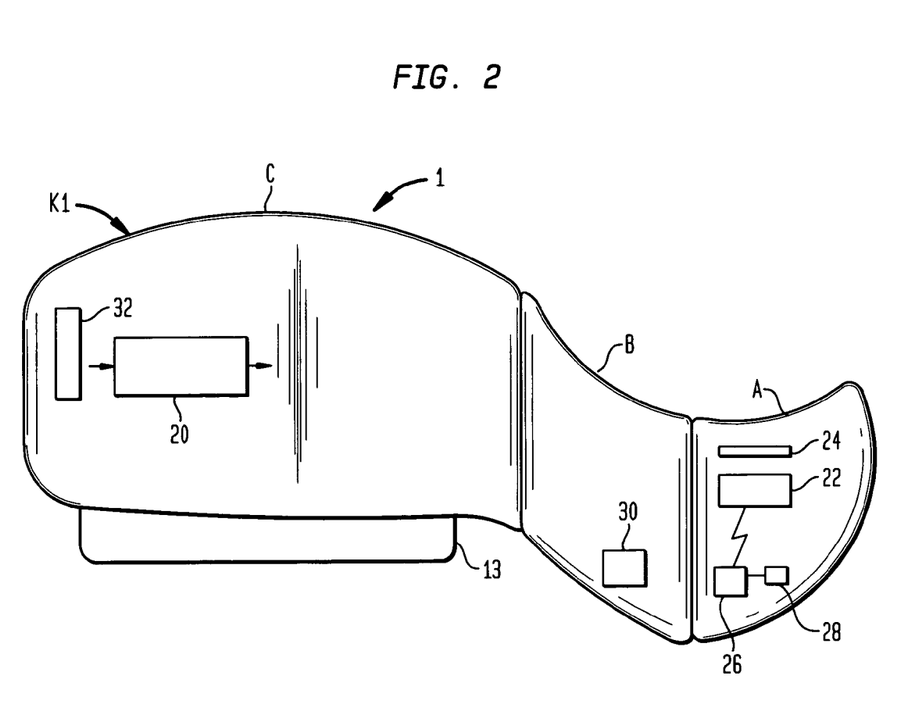
FIG. 2 is side, elevational, a sectional view of the artificial urinary diversion system shown in FIG. 1, taken along line II—II thereof.

FIG. 2 illustrates a lateral sectional view according to intersection II—II of FIG. 1. With this sectional view it can clearly be seen that the urinary diversion device 1 presented in FIG. 2 shows the topside of a first outline K1. Here, in contrast to FIG. 1, the elevation of the second area B to the bottom surface 7 of the first area A is more clearly seen. In this embodiment, a curved or curvilinear elevation is shown. This curved elevation serves to be brought into contact, for example, with the pubic bone and thus makes positional fixing possible. It can also be seen in FIG. 2 that below the third area so-called guide rails 13 are provided, in which a fixing element (not shown) can be inserted. At this point, special attention should be drawn to the fact that a protruding of the guide rails may, for example, be avoided by complete integration into the third area. While the activator or pump 20 is preferably contained in the third area C, when, for example, a screw pump 24 is utilized, it can be included in the first area A. In addition, a sphincter mechanism 22 for opening and closing the outlet 3 for the first area A is provided therein. Furthermore, by including a control system 26 in the device, the sphincter mechanism 22 can be controlled in order to regulate opening and closing thereof. Upon filling of the bladder, or upon the expiration of a predetermined time period, a signal 28 can be generated to advise the patient thereof. Upon receipt of such a signal, whether audible or seismic, the patient can regulate emptying of the bladder, so as to simulate everyday life as closely as possible. Optionally, a power supply 30 can also be included thereon, in order to achieve a highly compact and complete operating unit.

In addition, with the use of an anti-reflux device 32, such as appropriate valves and the like, the reflux of urine out of the device and into the kidneys can be prevented.

Figure 3:
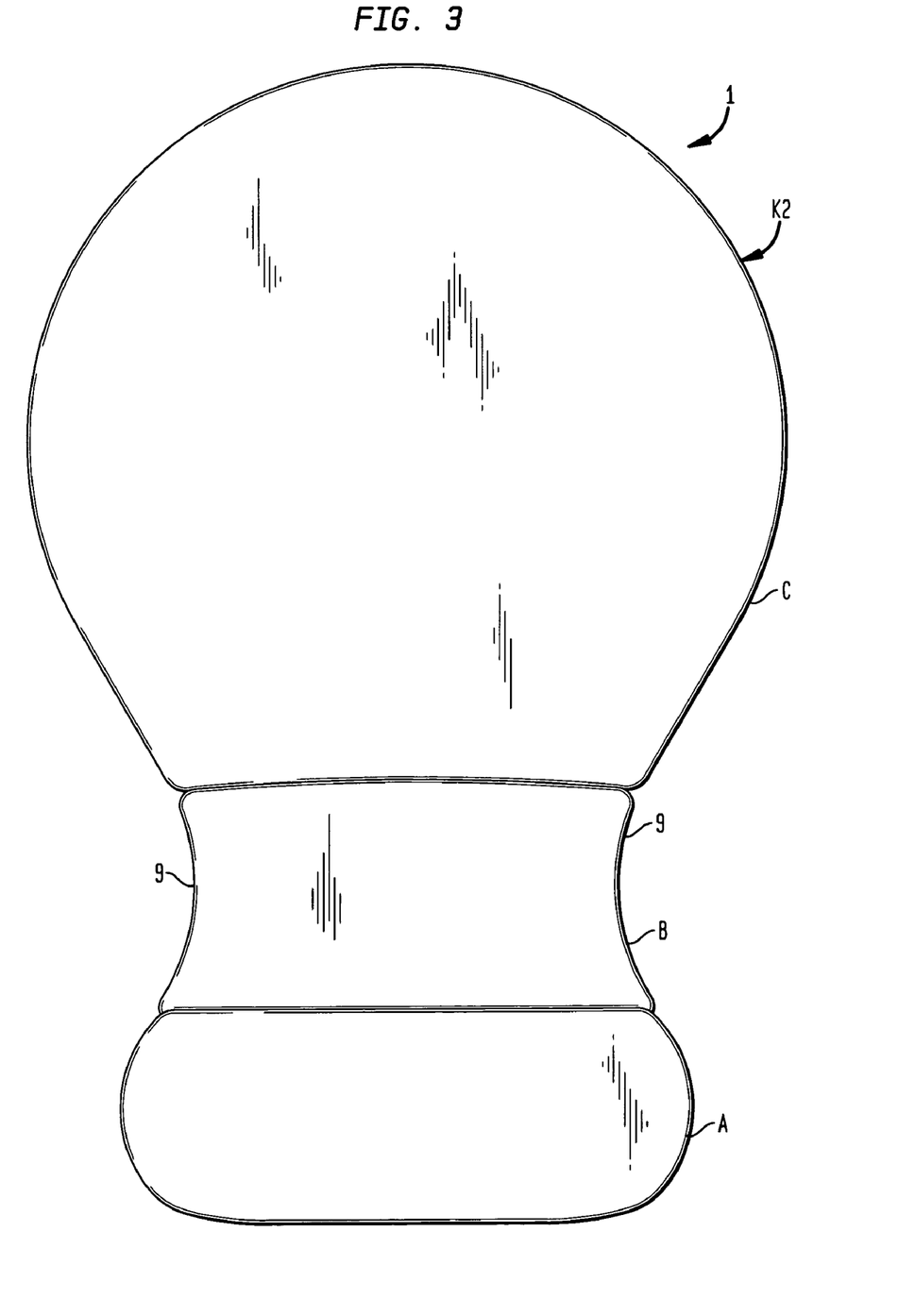
FIG. 3 is a top, elevational, view of the urinary diversion system shown in FIG. 1.

FIG. 3 illustrates a top view of the urinary diversion system 1 and a second outline K2 in accordance with FIG. 1, with the constriction caused by the second area B being clearly visible, such that the arteries can be led by laterally of the side surfaces 9. The relative proportions, which are shown between the first, the second and the third area, are also clearly visible.

Figure 4:
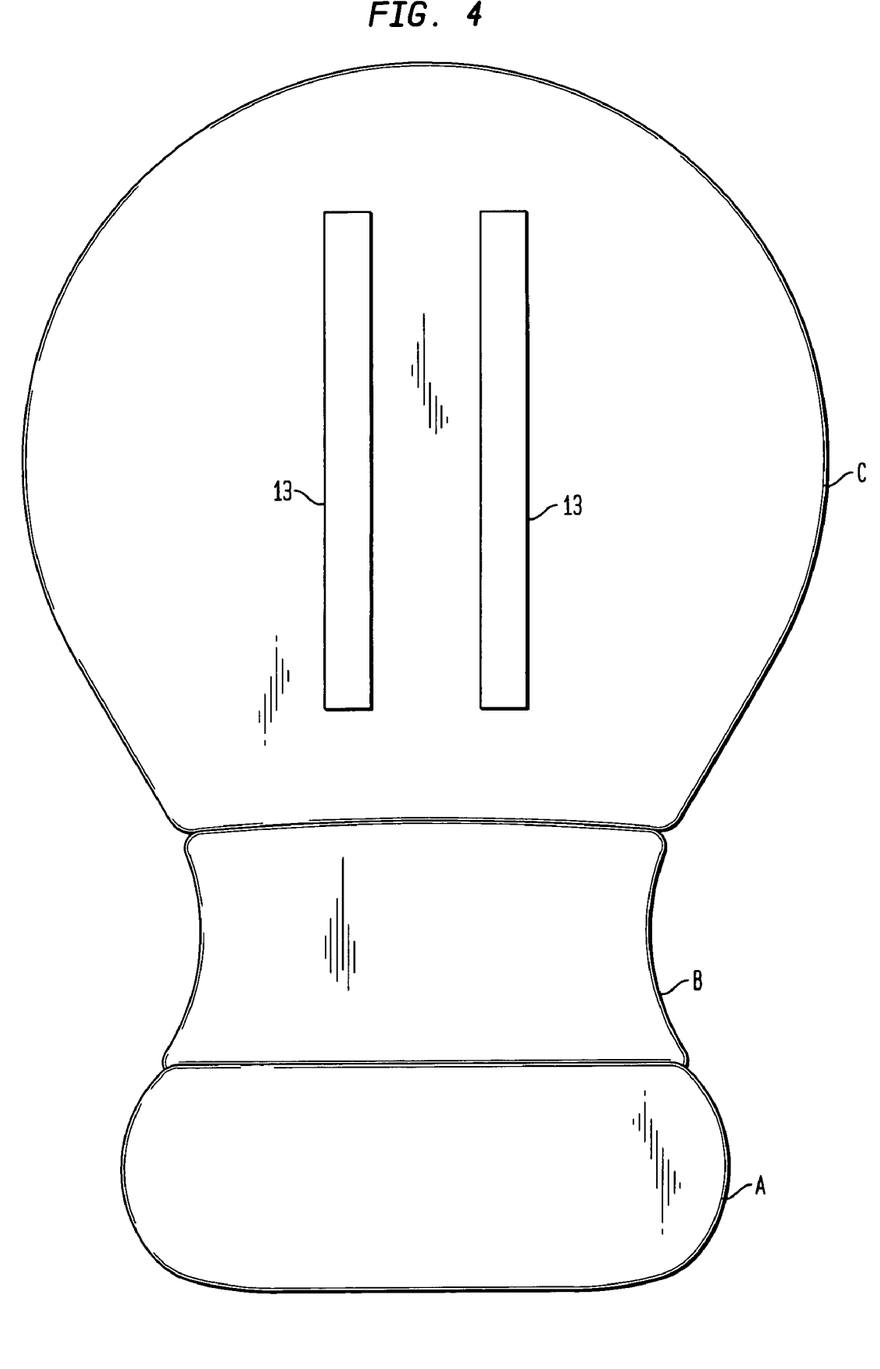
FIG. 4 is a bottom, elevational view of the urinary diversion system shown in FIG. 1.

FIG. 4 shows a bottom view of the urinary diversion system 1. The provided guide rails 13 for the fixing element are clearly indicated.

Figure 5:
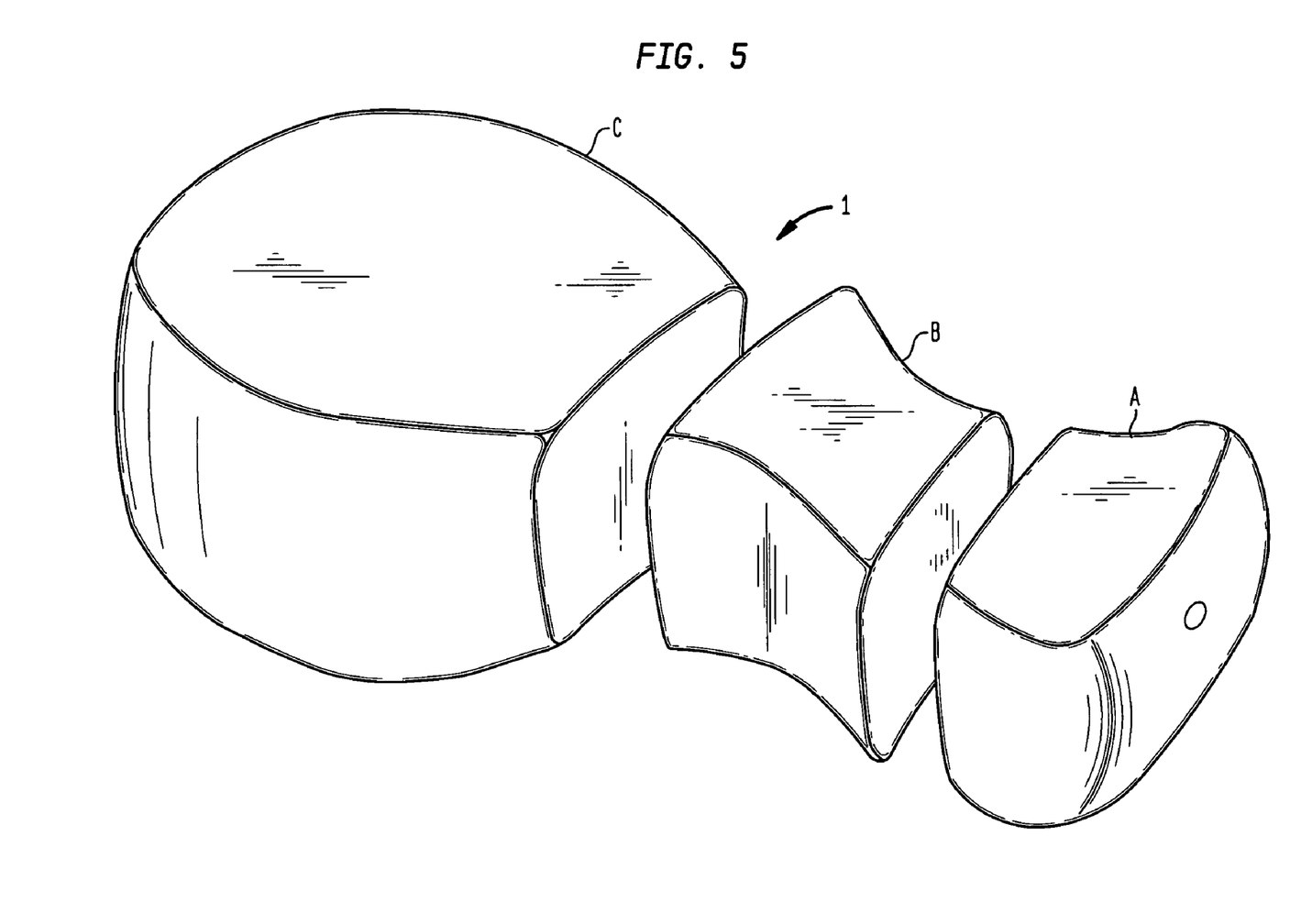
FIG. 5 is a side, perspective, fragmented view of the urinary diversion system shown in FIG. 1 separated into single areas.

FIG. 5 illustrates the urinary diversion system 1, with its individual areas, i.e. first, second and third area, illustrated separately.

At this point it should be noted that the division or sectioning into a first area, a second area and a third area sets forth a preferred embodiment hereof. The urinary diversion system can also be provided with only two areas or as an integral entity. On the other hand, it is also possible to provide more than three areas, which can be divided separately with more areas of the increased adapting variation being taken into account.

Figure 6:
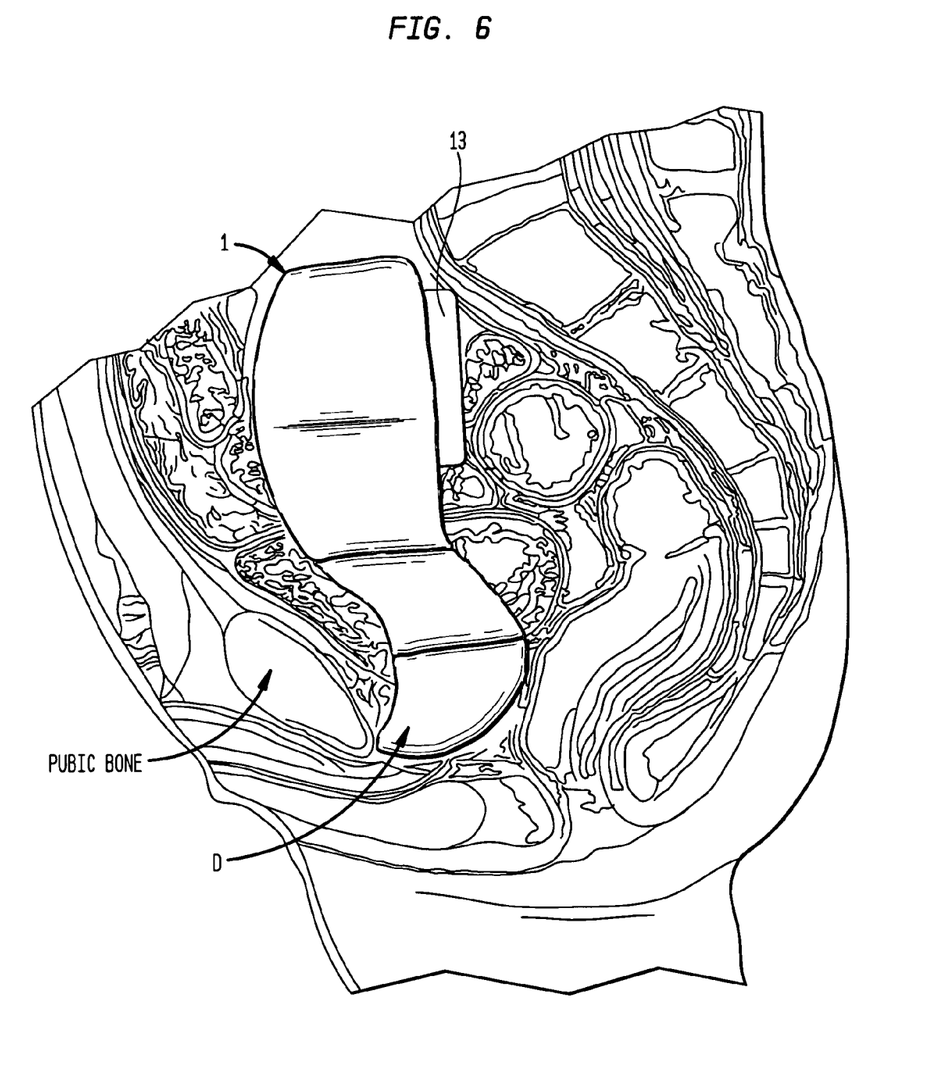
FIG. 6 is a side, elevational, sectional view of the arrangement of the urinary diversion system of the present invention in a human body.

FIG. 6 illustrates, for example, arranging of the urinary diversion system. The first area A borders on the pubic bone, with the fixing element, which is moveably includable in the guide rails, being fixed, for example, at the respective places in the abdominal cavity.

Figure 7:
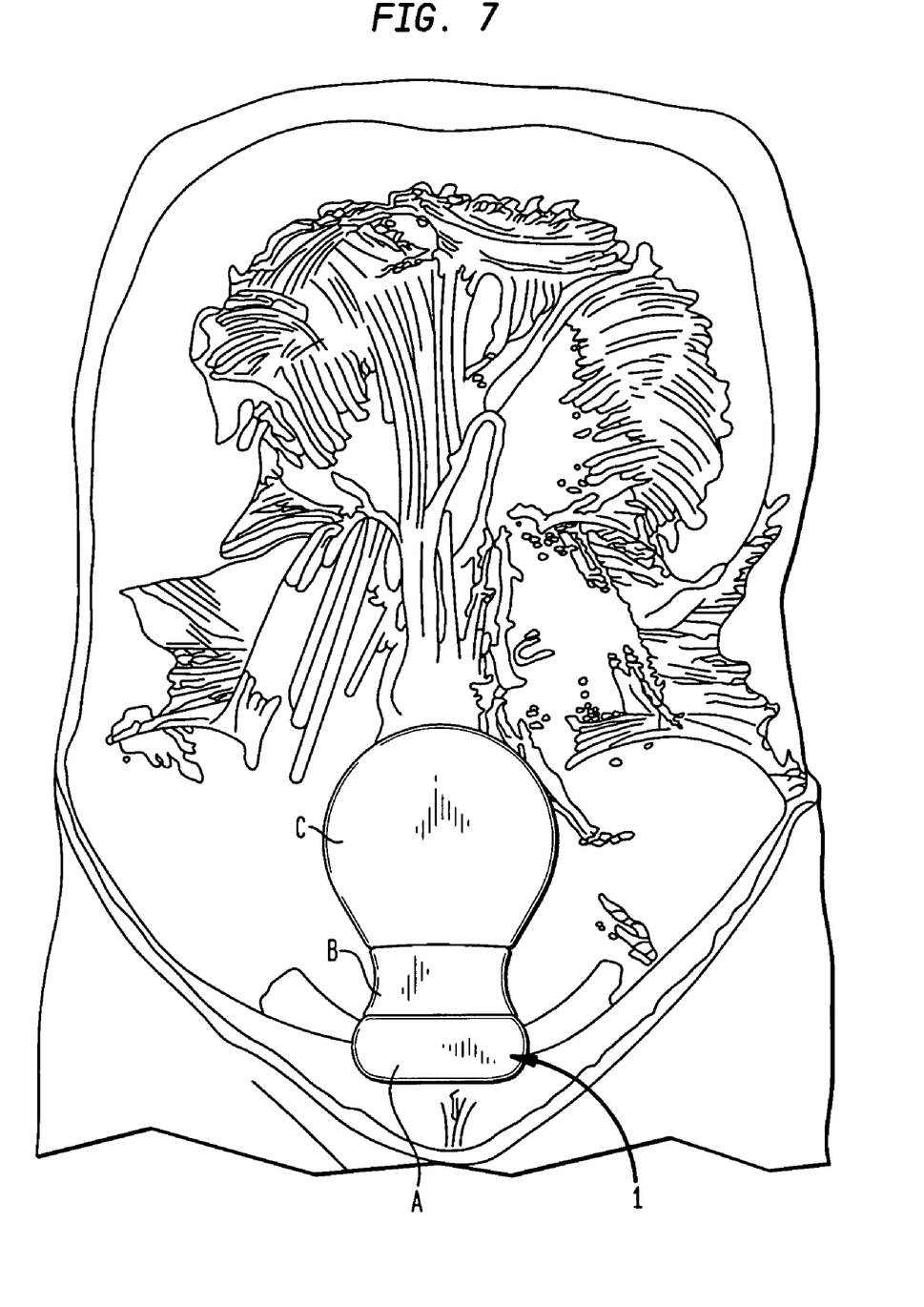
FIG. 7 is a front, elevational view of the urinary diversion system shown in FIG. 6.

FIG. 7 shows a front view for further illustration of arranging of the urinary diversion system hereof.

Figure 8:
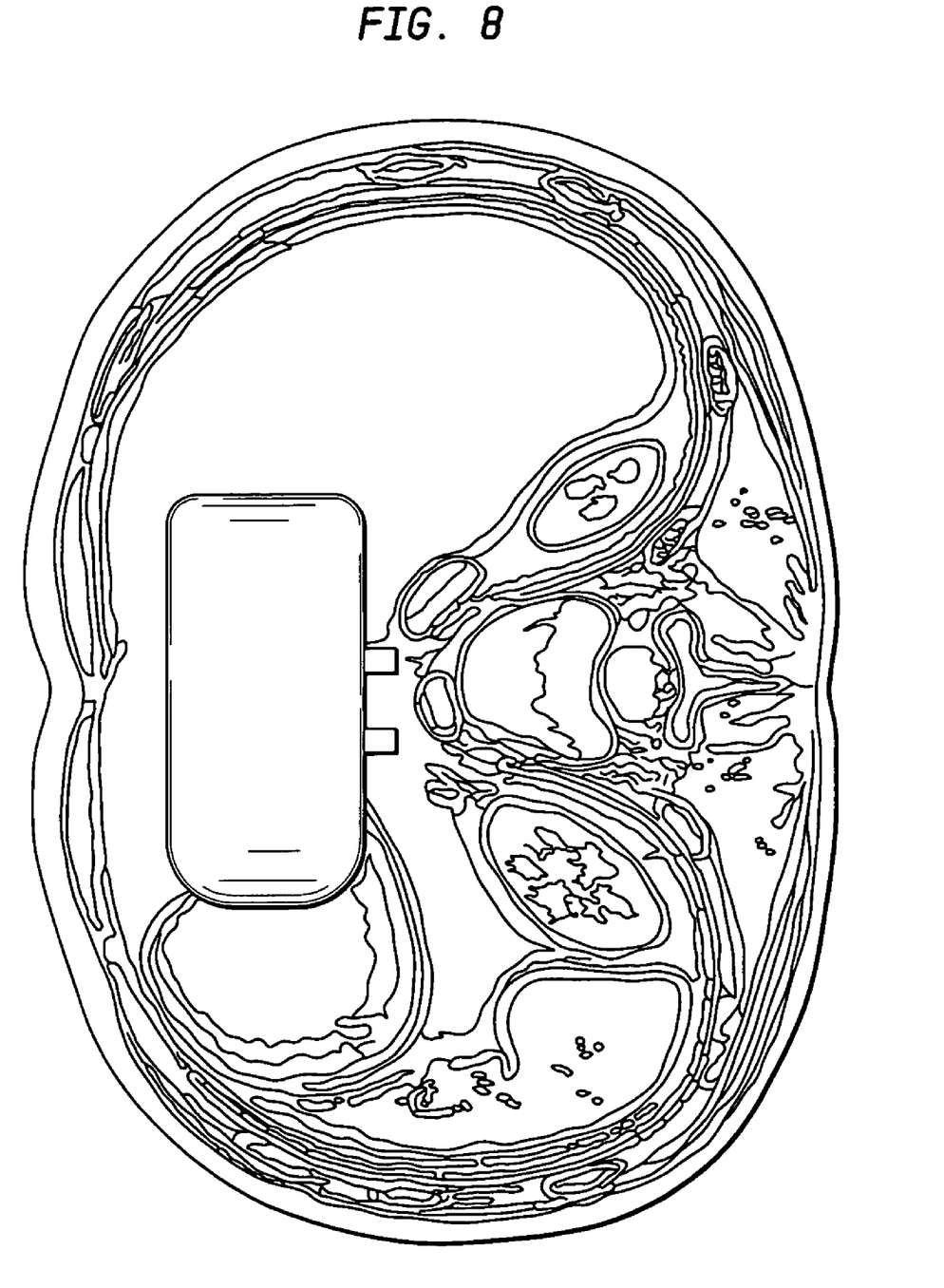
FIG. 8 is a top, elevational view of the urinary diversion system shown in FIG. 7, taken along line VII—VII thereof.

FIG. 8 is a top view, with the body section being above the section of said urinary diversion system.

Figure 9:
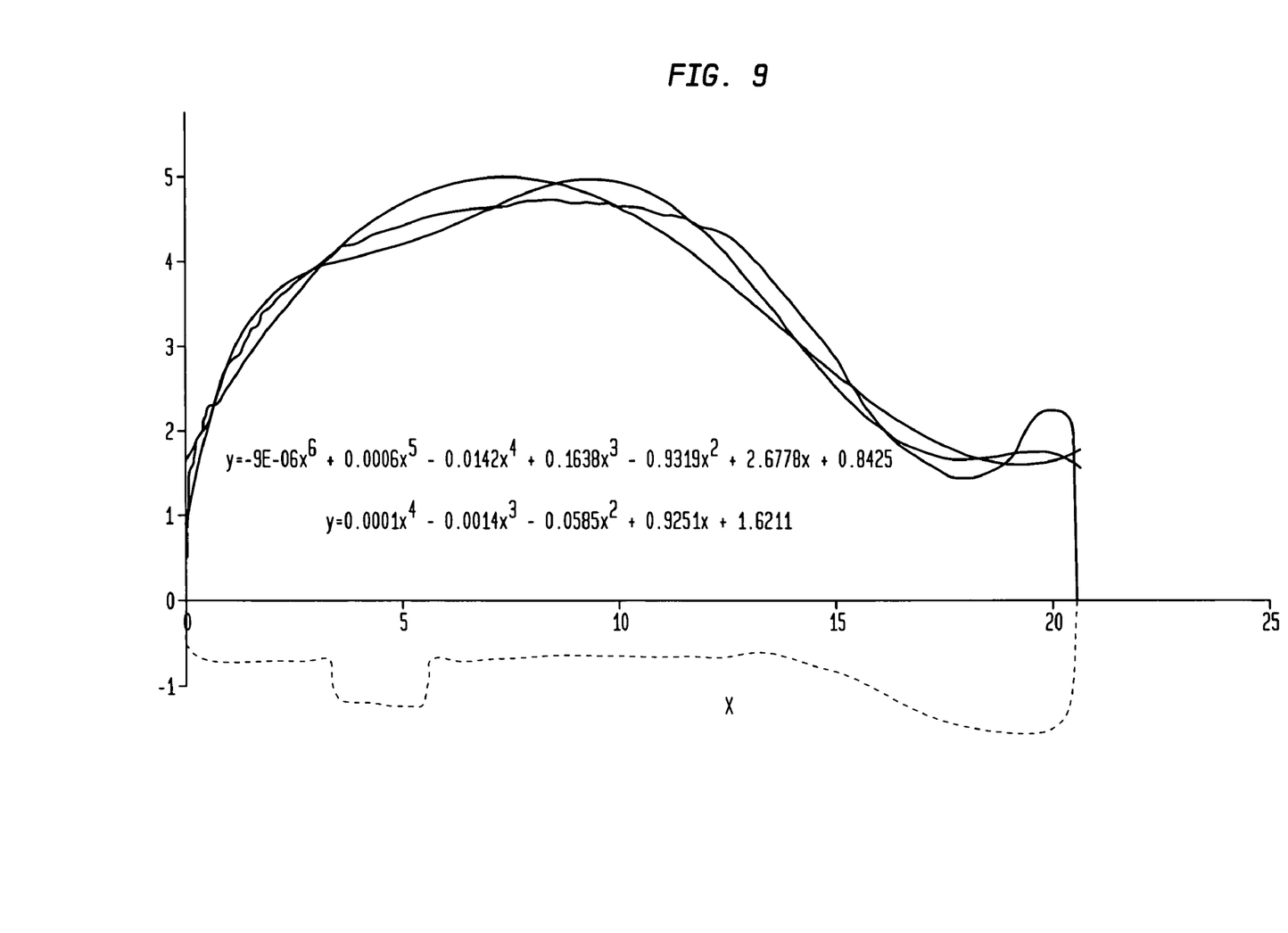
FIG. 9 is a graphical representation showing one executed polynomial function of $6^{th}$ degree regarding the top surface outline of the urinary diversion system in accordance with FIG. 1.

FIG. 9 is, for example, a fit curve of the polynomial form $f(x)=a_6x^6+a_5x^5+a_4x^4+a_3x^3+a_2x^2+a_1x+a$, i.e., a polynomial of $6^{th}$ degree, which has been adapted to the first outline. The parameters used for this adaptation are $a_6=-9\cdot10^6$; $a_5=0,006$; $a_4=-0,014$; $a_3=0,1638$; $a_2=-0,9319$; $a_1=2,6778$ and $a=0,8452$. However, it turned out that within a domain of $0\leq X\leq22$, the coefficients $a_1$ to $a_6$ in the domains $0<A<2$; $0<a_1<8$; $-2<a_2<0$; $0<a_3<1$; $-0,1<a_4<0$; $0<a_5<0,003$ and $-0,00001<a_6<0$ within a domain of $0<x<22$ can be taken.

Figure 10:
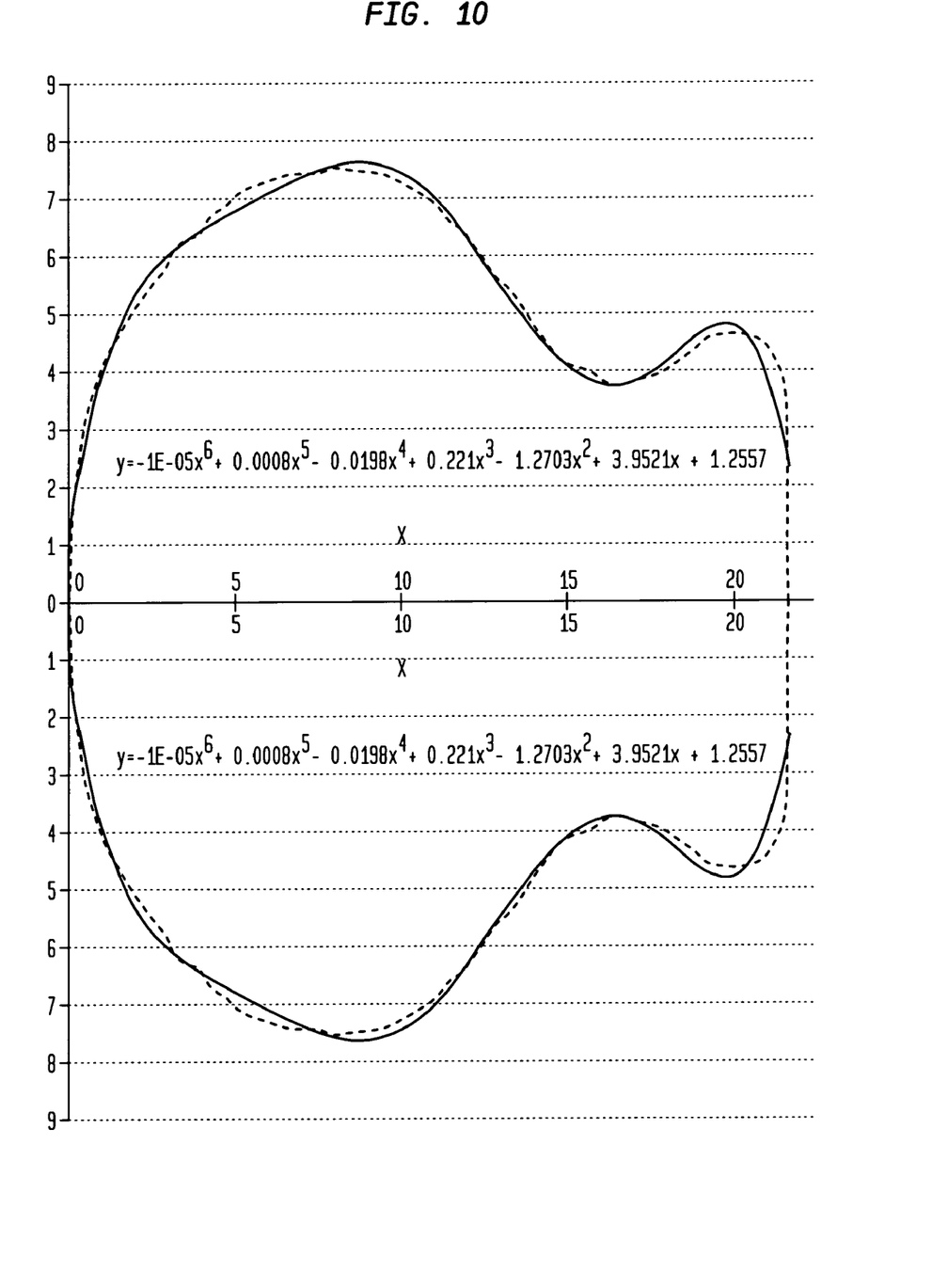
FIG. 10 is a graphical representation showing the top-view silhouette of the urinary diversion system shown in FIG. 1, relating to the polynomial function of $6^{th}$ degree referred to in FIG. 9.

FIG. 10 illustrates a top view of the half of a second outline, which has also been approximated with a polynomial of $6^{th}$ degree. The parameters used for this were $a_6=1\cdot10^{-5}$; $a_5=0,008$; $a_4=-0,0198$; $a_3=0,221$; $a_2=-1,2703$; $a_1=3,9521$ and $A=1,2557$. It has also been determined that these coefficients can also be taken in the domains $0<A<2$; $0<a_1<8$; $-2<a_2<0$; $0<a_3<1$; $-0,1<a_4<0$; $0<a_5<0,003$; and $-0,00001<a_6<0$ within a domain of $0<x<22$, for adapting the respective second outline. To illustrate that FIG. 10 is a top view, the first outline and the fitted curve have been reflected at y=0 at the x-axis of the diagram.

Figure 11:
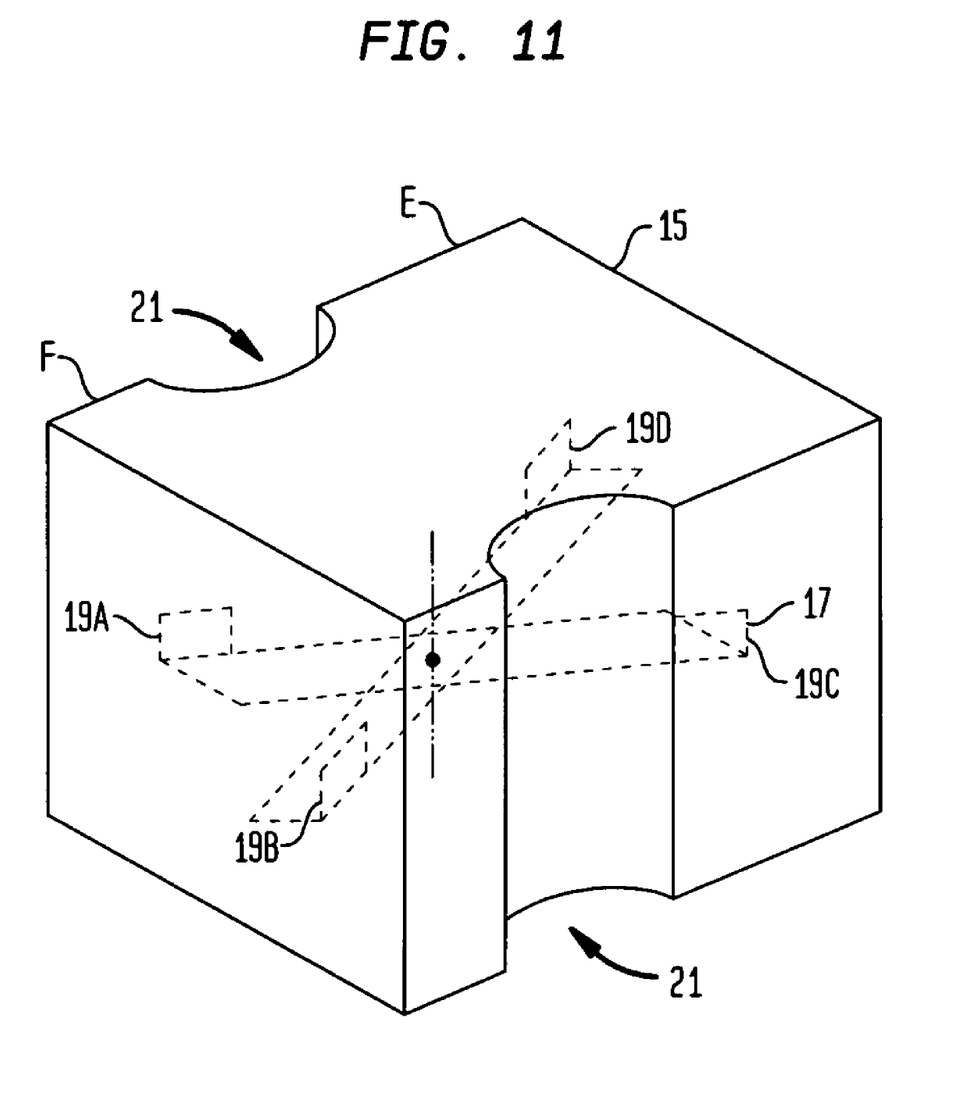
FIG. 11 is a side, elevational, schematic view of an embodiment of the fixing element used in accordance with the present invention.

FIG. 11 illustrates a fixing element 15 with a front area F, which can be introduced into the guide rails of the urinary diversion system, and an end area E, which can, for example, be pressed by hand.

Inside of the fixing element 15 there is a splay element (illustrated dashed), which is, due to the upright side surfaces 19A to 19D, taken along with the elastically formed fixing element 15 so that, for example, when impacting on the end area, the arms of the splay element 17 in the front area also move towards each other, and take the elastic material of the fixing element 15 with them.

Thus, the fixing element 15 can be narrowed such that it can be included between the two guide rails 13. After introduction, the fixing element 15 will be released, so that, due to the elasticity of fixing element 15, the front area F will return to its original shape, and a press fit/tight fit may be achieved with the side surfaces of the guide rails. If the fixing element 15 shall now be moved within the guide rail 13, it is only necessary to re-press or re-contract the end area E, in order to open the press fit of the side surfaces of the front area F. The slots or openings 21 in the fixing element 13 serve for being tightly led by the guide rails when the position of the fixing element is to be re-aligned.

Thus, with this fixing element 15 the urinary diversion device can be suitably arranged before its final arranging and the fixing element can be fixed at the corresponding position in the abdominal cavity.

Due to this additional provision, which is providing a fixing element that is separate from the urinary diversion system, it is also possible to pre-fix the fixing element at places difficult to access for fixing a fixing element, and to then introduce it into the urinary diversion device.

Instead of the screw pump, the pump using a telescope device, and the lever pump, all other types of pumps are imaginable for squeezing the urine, particularly a membrane pump or a gear pump.

The cross-sectional surfaces Q1, Q2 and Q3 can be different geometrical surfaces, such as quadratic, rectangular, trapezoidal, round, oval, elliptical or any other combination thereof.

Figure 12:
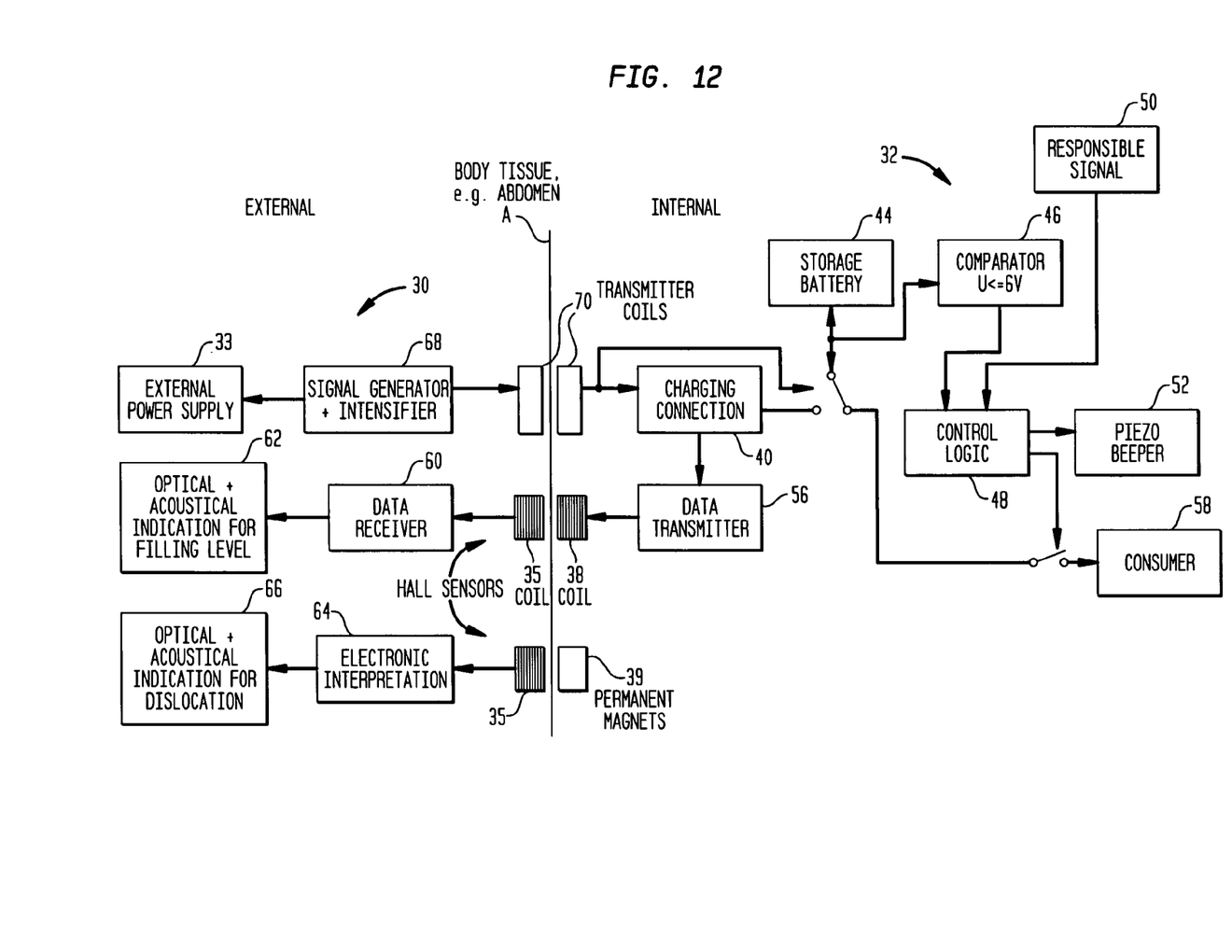
FIG. 12 is a schematic view of the dislocation unit of the present invention.

Exemplary for the block diagram, FIG. 12 shows electrical circuitry for the urinary diversion system with an external recharge unit and a dislocation unit. On the left side of the separating line A, the components of the recharge unit of the external power supply or of the dislocation unit are illustrated. On the right side of the separating line A, the components, which are linked to or integrated into the urinary diversion device are shown. In this embodiment, display of the dislocation is effected by an electronic evaluation of the Hall sensors, which are connected with the charging connection by means of a subcutaneous coil. The display of the charge status can, if possible, be effected optically or acoustically. The subcutaneously arranged components contain a charging connection, which is connected to the accumulator, when it is signalized by means of a control system signaling that the voltage has, for example, decreased for more than 6 volts, or it is signalized by means of a separate charge-status signal that the charging shall be effected. The charging connection is connected with a data-sender provider, which can, for example, indicate by means of the charging current if a dislocation is present. The control system particularly controls the status, when the consumer requires energy.

Figure 13:
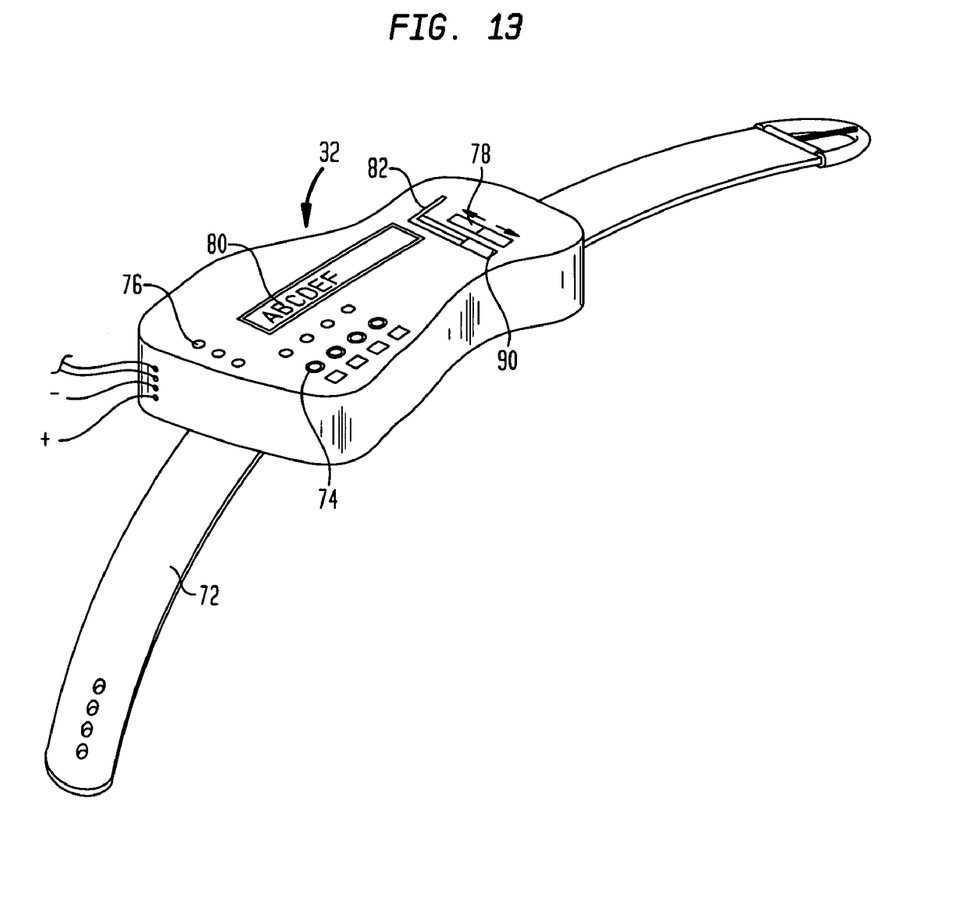
FIG. 13 is a side, perspective view of one embodiment of the dislocation unit of the present invention.

FIG. 13 shows an embodiment of a dislocation unit as an abdominal bandage with separate control, with the control containing a display for the longitudinal dislocation and for example a display for the rotational dislocation, preferably a level indicator. Basically, the control contains a longitudinal and rotational mobility possibility, which is relative to the fixing element, in this case a belt, in order to optimally position the dislocation unit. Furthermore, the control contains interrogation keys, by means of which it is possible to interrogate the recent operating state of the subcutaneously contained component. Furthermore, there is an LED display for the interrogation keys, with additional fix display modes being able to be made by means of the LED display.

Finally, concerning the spectroscopic examinations, it is noted that for the urinary diversion system, an emergency supply must be provided among all solutions of pumps, valves and anti-fix valves. This means that all artificial system components, such as valves, pumps, etc. have to be opened easily and to be easily movable or evadable. With this measure, the urinary diversion system will meet current medical standards.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An artificial urinary diversion device comprising a urinary bladder, having an axial direction and comprising at least one first portion having a plurality of first cross-sectional areas perpendicular to said axial direction defining both the outer surface and the inner volume of said first portion, said first portion including at least one largest first cross-sectional area and at least one outlet, a second portion having a plurality of second cross-sectional areas perpendicular to said axial direction defining both the outer surface and the inner volume of said second portion, said second portion including at least one largest second cross-sectional area, and a third portion having a plurality of third cross-sectional surfaces perpendicular to said axial direction defining both the outer surface and the inner volume of said third portion, said third portion including at least one largest third cross-sectional area, and at least one inlet for attachment to the renal urether of a patient, said second portion being arranged between said first portion and said third portion, said at least one largest third cross-sectional area being larger than said at least one largest second cross-sectional area, a sphincter mechanism for opening and closing said at least one outlet and being disposed in at least one of said first, second or third portions, control means for controlling said opening and closing of said sphincter mechanism for emptying said urinary bladder, and a pump for emptying said urinary bladder, said pump being entirely enclosed within said first, second or third portions of said artificial urinary diversion device.

2. The artificial urinary diversion device according to claim 1 wherein said first, second and third portions comprise modular units, whereby each of said first, second and third portions includes a transitional surface permitting a continuous surface transition between said modular units.

3. The artificial urinary diversion device according to claim 1 including at least one anti-reflux valve.

4. The artificial urinary diversion device according to claim 3 wherein said at least one anti-reflux valve is disposed in said third portion.

5. The artificial urinary diversion device according to claim 1 wherein said first, second and third portions are formed integrally.

6. The artificial urinary diversion device according to claim 1 including expulsion means for expelling liquid from said apparatus.

7. The artificial urinary diversion device according to claim 1 wherein said third portion includes a pair of said inlets.

8. The artificial urinary diversion device according to claim 1 wherein said sphincter mechanism and said control means are disposed entirely within said artificial urinary diversion device.

* * * * *